United States Patent [19]

Allen, Jr. et al.

[11] Patent Number: 4,660,147

[45] Date of Patent: Apr. 21, 1987

[54] METHOD FOR DETERMINING LEVEL OF FINISH AND CONTROL THEREOF

[75] Inventors: John L. Allen, Jr., Charlotte; Teddy H. Grandstaff, Kinston, both of N.C.

[73] Assignee: E. I. du Pont de Nemours and Company, Wilmington, Del.

[21] Appl. No.: 768,699

[22] Filed: Aug. 23, 1985

[51] Int. Cl.⁴ .................. G06F 15/46; B05D 1/00; B05C 11/00
[52] U.S. Cl. ........................................ 364/468; 427/9; 427/10; 118/665; 118/674
[58] Field of Search ............... 364/468, 200, 900; 427/9, 10, 365, 389.9, 174, 175; 118/665, 672, 674; 361/170

[56] References Cited

U.S. PATENT DOCUMENTS

| | | | |
|---|---|---|---|
| 3,207,125 | 9/1965 | Strandberg, Jr. | 118/664 |
| 3,927,356 | 12/1975 | Hodson et al. | 361/170 |
| 4,345,205 | 8/1982 | Sung | 118/665 X |
| 4,358,473 | 11/1982 | DeBott et al. | 427/10 |
| 4,370,210 | 1/1983 | Yoshihara et al. | 427/10 |
| 4,370,355 | 1/1983 | Niesse | 427/10 |
| 4,479,979 | 10/1984 | Prober | 427/9 |

Primary Examiner—Gary V. Harkcom
Assistant Examiner—Jon D. Grossman

[57] ABSTRACT

A method of controlling the flow of finish to a moving synthetic fibrous tow involves continuous non-contact monitoring of electrostatic voltage (ESV), tow speed and temperature by appropriate sensors which are interfaced with a computer that provides continuous computation of percent finish on the tow. Out of limit signals are relayed to the point of finish application to adjust the amount of finish being applied to the tow.

7 Claims, 6 Drawing Figures

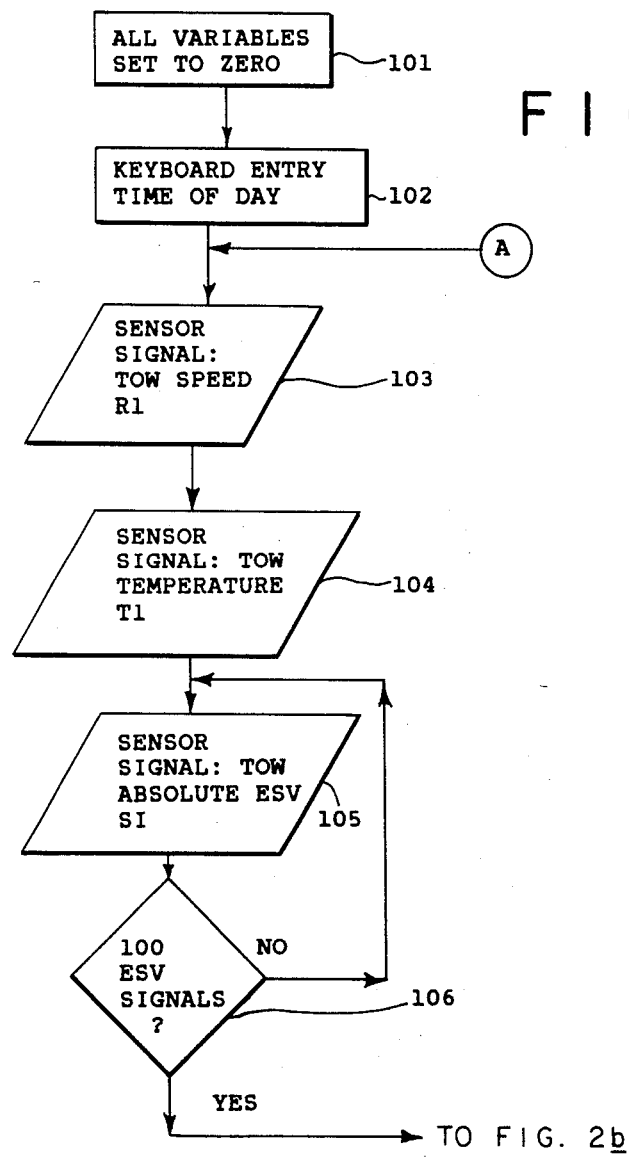

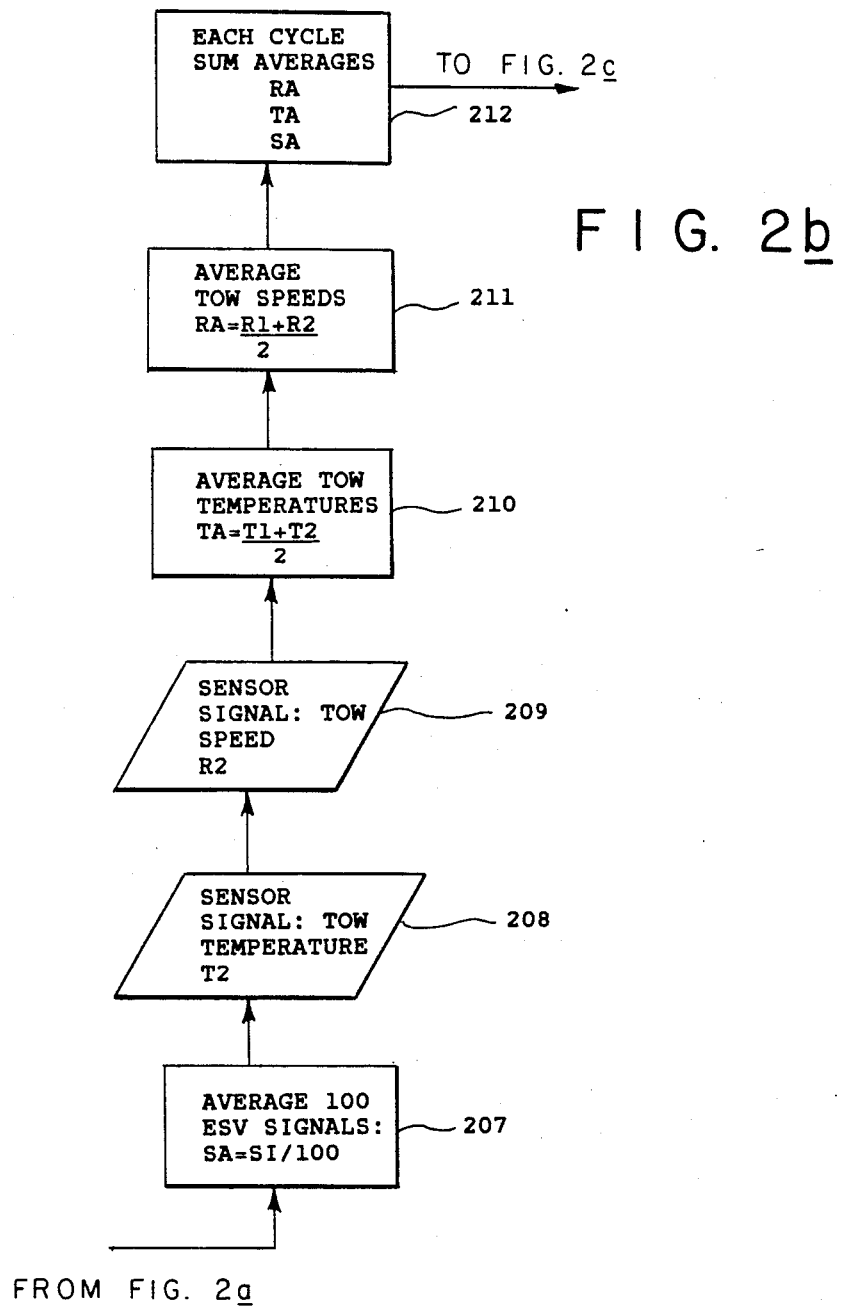

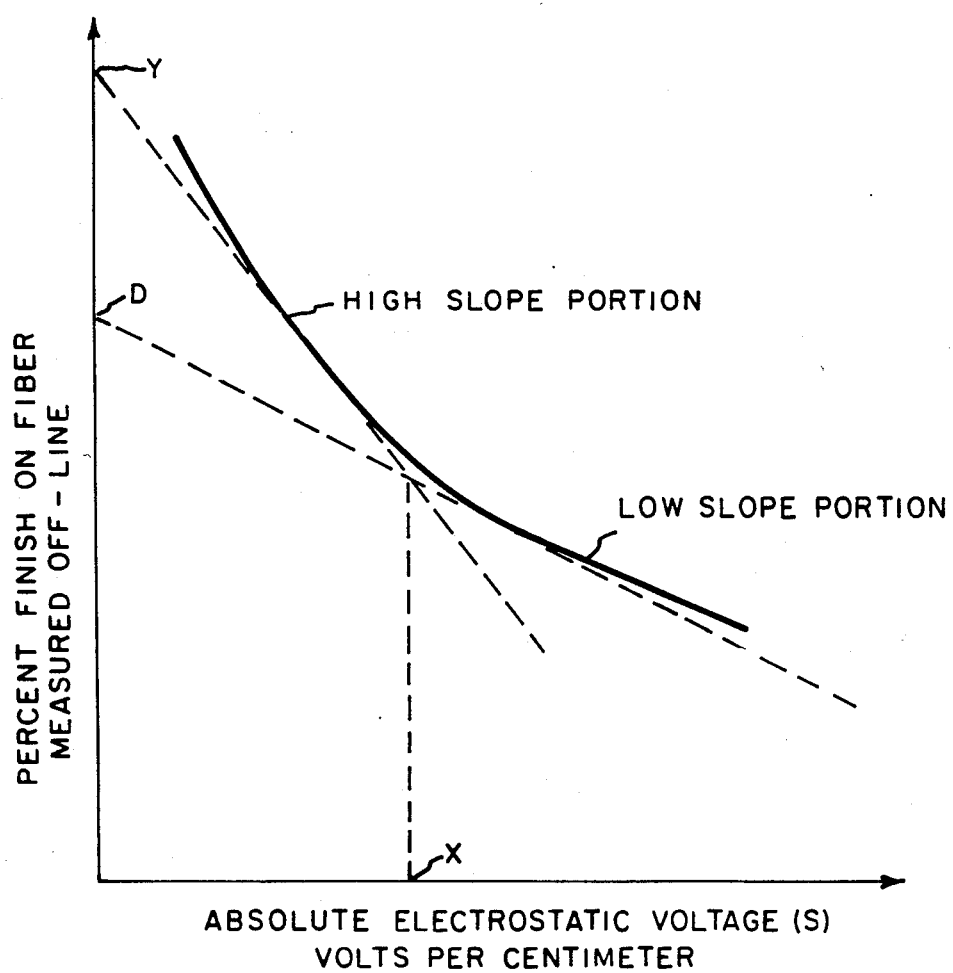

METHOD FOR DETERMINING LEVEL OF FINISH AND CONTROL THEREOF

BACKGROUND OF THE INVENTION

This invention relates to a method for determining finish level on a moving synthetic polymeric material, more particularly, it relates to determining such finish levels on filaments by monitoring electrostatic voltage(s) (ESV) on filaments gathered into a tow.

Substances known as finishes are usually applied to synthetic polymeric filaments for lubrication to reduce friction as they advance over guides, draw pins and other machine elements in various filament handling processes. Finishes may also be applied to reduce the generation of static electricity, conduct such charges away, or provide soil or stain resistance capability to the yarn.

If the supply or application of finish is interrupted, increased or reduced, the filament handling process may break down or the product may be unsatisfactory to the customer. Since finishes are usually colorless, the absence of finish even on the outside of a filament package is difficult to detect, and a temporary finish interruption is usually not detected.

Methods for detecting the presence or absence of finish are known, employing instruments which respond to some characteristic of the finish such as conductance. However, such devices are often quite expensive, difficult to maintain and are usually not applicable to on-line real time finish monitoring.

SUMMARY OF THE INVENTION

It has now been found that finish levels may be detected without contacting the filaments by monitoring the ESV on the filaments. The practice has been found to be useful in monitoring finish levels on tow formed from polyester filaments. The method involves continuous on-line, non-contact monitoring of a synthetic fiber tow during production while the tow is moving through the production steps to measure ESV on the tow along with speed, and tow temperature. Sensors for these measurements are interfaced with a computer which provides a continuous computation of percent finish level on the tow. Out of limits signals generated by the computer are used to adjust the amount of finish being applied.

BRIEF DESCRIPTION OF THE DRAWINGS

FIGS. 2a, 2b, 2c are logic flow diagrams for the computer.

FIG. 3 is a plot of percent finish on fiber measured off-line vs. absolute ESV, S, measured during production at a tow speed, M, and a tow temperature, Q.

DETAILED DESCRIPTION OF THE PREFERRED EMBODIMENT

Figure 1:
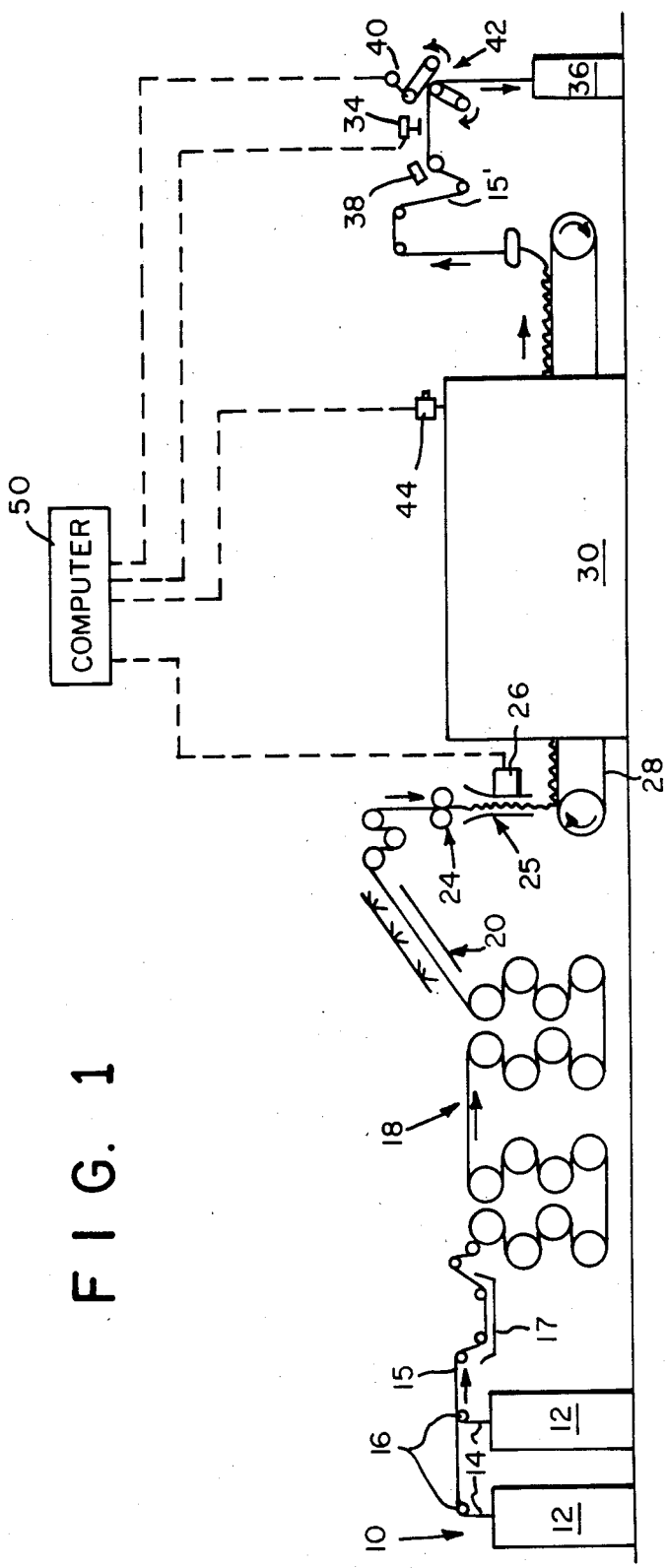
FIG. 1 shows, schematically, a tow production process and the locations where an ESV detector, a tachometer and a temperature sensor may be placed with the signals from these sensors interfaced with a computer.

Referring to FIG. 1, the embodiment chosen for purposes of illustration includes a creel 10 filled with cans 12 of undrawn, continuous filament bundles 14, which are formed into a tow 15. A finish has been applied during spinning to these bundles to give sufficient cohesion for control while pulling through the creel guides 16 to the draw machine generally designated 18. The undrawn tow 15 is pulled first through a prefeed pan 17 and then into the draw zone where it is flooded with water or aqueous finish and stretched to achieve the desired draw ratio. The drawn tow goes through a chute 20 where finish is applied by spray applicators (not shown) and on into the crimper 24. Much of the finish applied in chute 20 is squeezed out of the tow during the crimping step in crimper 24. To make up for this loss of finish a post crimper finish is sprayed onto the tow as it passes through lay-down chute 25 by means of spray applicator 26. It is the rate of this post crimper finish application that the on-line finish monitor should control to maintain the goal level on the final product. The drawn, crimped tow leaves crimper 24 and is deposited from the lay-down chute 25 onto a conveyor belt 28. The conveyor belt transports the tow into an oven 30 where it is dried. The tow is then transported by the conveyor belt out of the oven and pulled past the ESV sensor 34 and deposited in a box 36.

In the event that the charge level on the filaments is insufficient for the ESV sensor 34 to detect, an ion generator 38 may be used to apply additional charge to the filaments.

Signals generated by ESV sensor 34, tachometer 40 coupled to puller belts 42 for sensing tow speed, and infra-red temperature sensor 44 are sent to computer 50 which continuously calculates the percent finish level on the tow 15'. Out of limit signals generated by the computer are used to adjust the amount of finish being applied to the tow by increasing or decreasing the rate of finish concentrate addition to the liquid applied in the draw machine 18 and/or the rate of finish application to the tow after drawing, i.e., via applicator 26 on chute 25.

The control components of the apparatus are commercially available items. Typical components are as follows:

| ELEMENT NUMBER | ELEMENT NAME | COMMERCIAL IDENTIFICATION |
|---|---|---|
| 26 | applicator | turbine meter Model No. FTO-N-5-L-JS, Flow Technology, Inc. controller Model No. 350CST Moore, Inc. control valve Model MicroPack (CV = 0.60) Masoneilan, Inc. spray nozzle Unijet Type ¼TT, Spraying System, Inc. |
| 34 | ESV sensor | Model No. 1 Allen Science Research (ASR) Inc. Charlotte, NC |
| 38 | ion generator | Model No. 2, ASR, Inc. Charlotte, NC |
| 40 | tachometer | Model No. 5AN102A01G0201 By General Electric |
| 44 | infra-red temperature sensor | Modline Series 3400 Radiation Thermometer Ircon, Inc., Skokie, IL. |
| 50 | computerized controller with ana- | Model No. 1, ASR, Inc. Charlotte, NC |

| ELEMENT NUMBER | ELEMENT NAME | COMMERCIAL IDENTIFICATION |
|---|---|---|
| | -continued | |
| | log input/output | |

The equation used by the computer to determine percent finish on fiber is:

If $W < X$ then $P = Y - (U)(W)$

If $W = > X$ then $P = D - (N)(W)$ where:

$$W = \frac{(M)(H - Q)(S)}{(E)(H - Z)}$$

M = the calibration tow speed, i.e., the preferred speed for the particular tow product,
H = the extrapolated value for tow temperature corresponding to zero absolute ESV at tow speed M and the preferred finish application rate (FIG. 4),
Q = the calibration tow temperature, i.e., the preferred temperature for the particular tow product,
S = the average of 1000 absolute ESV signals (FIGS. 2a, 2b, 2c),
Z = the average of 20 tow temperature signals (FIGS. 2a, 2b, 2c),
E = the average of 20 tow speed signals (FIGS. 2a, 2b, 2c),
X = the absolute ESV value at which the percent finish on fiber vs. absolute ESV calibration curve changes slope most rapidly (FIG. 3),
D = percent finish on fiber axis intercept of tangent to the low slope portion of the percent finish on fiber vs. absolute ESV calibration curve (FIG. 3),
N = slope of the low slope portion of the percent finish on fiber vs. absolute ESV calibration curve,
Y = percent finish on fiber axis intercept of tangent to the high slope portion of the percent finish on fiber vs. absolute ESV calibration curve (FIG. 3),
U = slope of the high slope portion of the percent finish on fiber vs. absolute ESV calibration curve, and
P = the computed percent finish on fiber.

Figure 4:
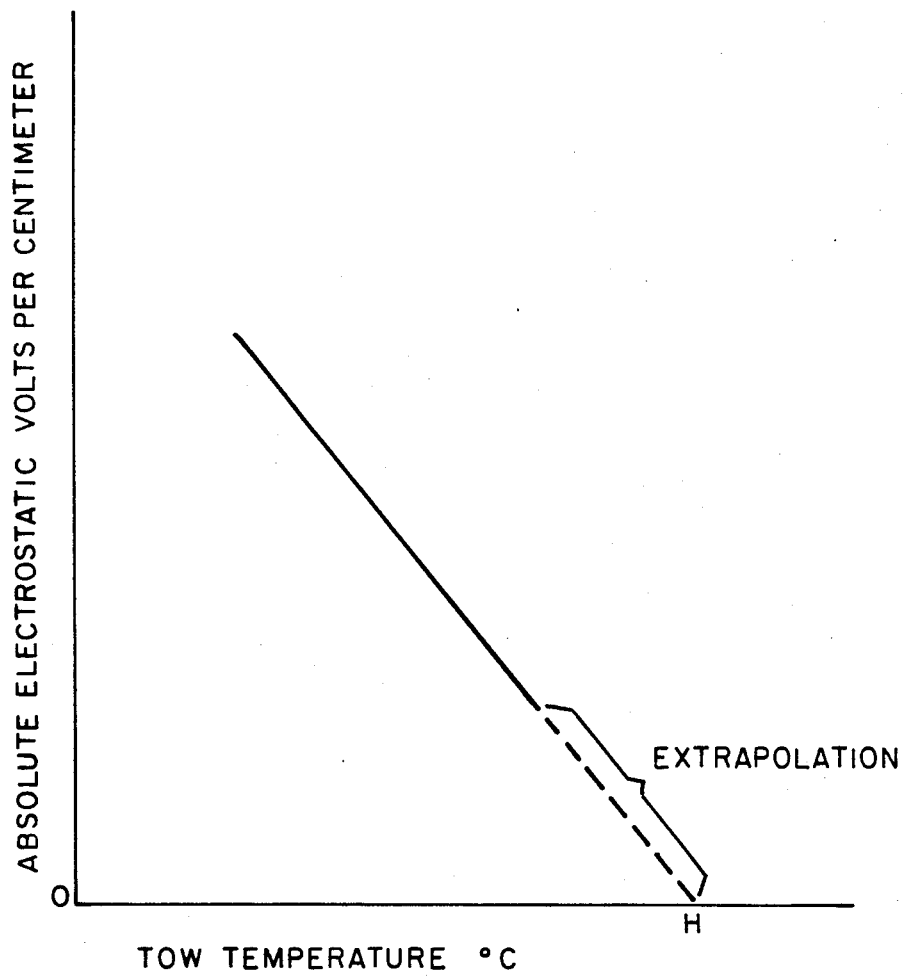
FIG. 4 is a plot of absolute ESV as a function of tow temperature for tow drawn with a preferred level of finish at the calibration speed M.

The first step in developing the equation is to measure absolute ESV during product drawing with various finish application rates at tow speed (M) and tow temperature (Q). M and Q are the preferred values for the process. Tow samples are taken at each finish application rate and percent finish on fiber is measured off-line. The finish application rate scan should cover the range that might be encountered during production. A plot is then made of percent finish on fiber opposite absolute ESV (S) as shown in FIG. 3. At tow speed (M) and the nominal finish application rate expected for the process, the tow temperature is changed over the range anticipated for the process and the absolute ESV measured at selected temperatures. A plot of absolute ESV vs. tow temperature is then made and extrapolated to zero absolute ESV (FIG. 4). The tow temperature corresponding to zero absolute ESV obtained is designated H. The values of M, H, Q, X, D, N, Y and U are obtained during calibration.

Figure 2C:
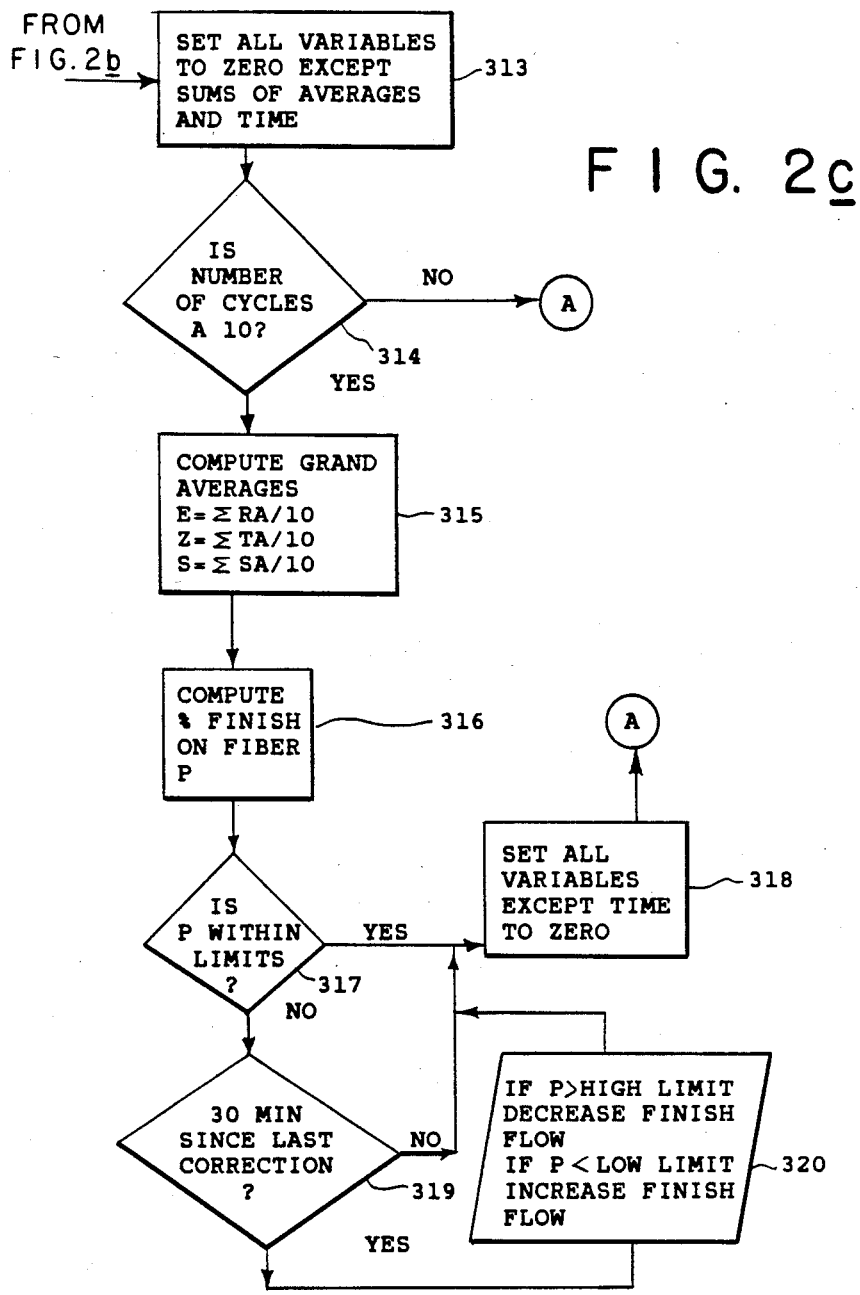

The logic for automatic control of the finish applied to the tow at the lay-down chute 25 is shown by the software flow charts in FIGS. 2a, 2b and 2c. More particularly, the computer sets all variables to zero when turned on (101). The time of day is entered at the keyboard (102). This sets and starts the clock in the computer. Tow speed and temperature signals ($R_1$ and $T_1$ respectively) from sensors 40, 44 respectively are received and stored by the computer (103) and (104). An ESV signal (SI) from the sensor 34 is received and stored by the computer; all ESV signals, plus and minus, are treated as plus values (105), i.e., absolute ESV values. The computer accepts and stores ESV signals until 100 signals have been received (106) then goes to the next step (207) where the average of the 100 ESV signals (SA) is computed and stored. Tow speed and tow temperature signals ($R_2$ and $T_2$ respectively) are received and stored again by the computer (208) and (209). The average of the first and the second tow temperature signals (TA) is computed (210) and the average of the first and the second tow speed signals (RA) is computed (211). These averages are stored. The computer keeps a running total of average tow speed, tow temperature, the tow ESV (212). In the next step (313), all variables except the running totals and time are set to zero. The computer determines if the sequence of steps from point A has been cycled through 10 times (314). If not, the computer returns to point A and another cycle is completed. When 10 cycles have been repeated, each of the running totals, i.e., $\Sigma RA$, $\Sigma TA$, $\Sigma SA$ as in FIG. 2c is divided by 10 to produce the grand average tow speed E, the grand average tow temperature Z, and the grand average ESV (S) (315) (FIG. 2c). The percent finish on fiber P is then computed (316) by use of equations previously presented. The percent finish on fiber is compared with the high and low limits that are constants included in the software (317). If the percent finish is within limits, the computer goes back to point A in the program after setting all variables to zero except time (318). If the percent finish is not within limits, the computer determines whether or not 30 minutes have passed since the last finish application adjustment was made (319). If not, the computer goes back to point A in the program after setting all variables to zero except time (318). If 30 minutes have passed since the last finish application adjustment, the computer, via applicator 26, decreases finish application if the percent finish is greater than the high finish limit and increases finish application if percent finish is less than the low finish limit (320).

What is claimed is:
1. A method of controlling flow of finish to a moving fibrous material to maintain the percent finish on fiber within upper and lower limits with a computer, comprising:
(a) providing the computer with a data base for percent finish on fiber including at least,
calibration material speed (M),
calibration material temperature (Q),
slope (n) of the low slope portion of the percent finish on fiber v. absolute electrostatic voltage calibration curve
a slope (u) of the high slope portion of the percent finish on fiber vs. absolute electrostatic voltage calibration curve,
a percent finish on fiber axis intercept (D) of tangent to the low slope portion of the percent finish on fiber vs. absolute electrostatic voltage calibration curve,
a percent finish on fiber axis intercept (Y) of tangent to the high slope portion of the percent finish on fiber vs. absolute electrostatic voltage calibration curve, absolute electrostatic voltage value (x) which represents a point at which said fiber axis intercept (d) intersects said fiber axis intercept (y), an extrapolated value (H) for tow temperature corresponding to zero absolute electrostatic voltage at calibration material speed (M) and a preferred finish application rate, (b) repetitively determining the material speed, temperature and absolute electrostatic voltage on said material as it moves past the respective sensor locations;

(c) repetitively providing the computer with the material speed, temperature and absolute electrostatic voltage signals for averaging to determine material speed, material temperature and absolute electrostatic voltage grand averages E, Z, S respectively;

(d) repetitively calculating in the computer at frequent intervals percent finish on fiber using the equations IF $W = X$ then $P = Y - (U)(W)$ IF $W = > X$ then $P = D - (N)(W)$ where:

$$W = \frac{(M)(H - Q)(S)}{(E)(H - Z)};$$

(e) repetitively comparing in the computer at said frequent intervals as said material moves past said sensor location percent finish on fiber (P) with said upper and lower limits; and (f) controlling said flow of finish according to the value of P.

2. The method of claim 1 wherein said fibrous material is polyester filamentary material.

3. The method of claim 2 wherein said polyester filamentary material is a tow.

4. The method of claim 1 wherein said flow of finish is increased if percent finish on fiber is less than said lower limit.

5. The method of claim 1 wherein said flow of finish is decreased if percent finish on fiber is greater than said upper limit.

6. The method of claim 1, including the step of signalling when P is less than said lower limit or when P is greater than said upper limit.

7. The method of claim 1, including the step of displaying the value of P.

* * * * *